US010981832B2

(12) United States Patent
Iwamoto et al.

(10) Patent No.: US 10,981,832 B2
(45) Date of Patent: Apr. 20, 2021

(54) SINTERED CALCIUM PHOSPHATE MOLDED BODY AND PROCESS FOR MANUFACTURING THE SAME

(71) Applicant: SofSera Corporation, Tokyo (JP)

(72) Inventors: Takashi Iwamoto, Tokyo (JP); Yasumichi Kogai, Tokyo (JP); Karl Kazushige Kawabe, Tokyo (JP)

(73) Assignee: SofSera Corporation, Tokyo (JP)

( * ) Notice: Subject to any disclaimer, the term of this patent is extended or adjusted under 35 U.S.C. 154(b) by 259 days.

(21) Appl. No.: 15/760,177

(22) PCT Filed: Sep. 7, 2016

(86) PCT No.: PCT/JP2016/076347
§ 371 (c)(1),
(2) Date: Mar. 14, 2018

(87) PCT Pub. No.: WO2017/047474
PCT Pub. Date: Mar. 23, 2017

(65) Prior Publication Data
US 2019/0177228 A1 Jun. 13, 2019

(30) Foreign Application Priority Data

Sep. 16, 2015 (JP) .................................. 2015-183414

(51) Int. Cl.
*C04B 35/447* (2006.01)
*C01B 25/32* (2006.01)
(Continued)

(52) U.S. Cl.
CPC ............ *C04B 35/447* (2013.01); *A61L 31/00* (2013.01); *B01J 20/04* (2013.01); *B01J 20/30* (2013.01);
(Continued)

(58) Field of Classification Search
None
See application file for complete search history.

(56) References Cited

U.S. PATENT DOCUMENTS 3,485,777 A * 12/1969 Gaylord .................... C08L 3/02
524/35
6,235,225 B1 5/2001 Okada et al.
(Continued)

FOREIGN PATENT DOCUMENTS

| JP | H02-14866 A | 1/1990 |
| JP | H02-51466 A | 2/1990 |

(Continued)

OTHER PUBLICATIONS

Lungan et al. Surface characterization and drug release from porous microparticles based on methacrylic monomers and xanthan. Carbohydrate Polymers 125 (Jul. 10, 2015) 323-333. (Year: 2015).*
(Continued)

*Primary Examiner* — Erin Snelting
(74) *Attorney, Agent, or Firm* — Osha Bergman Watanabe & Burton (57) ABSTRACT

To provide a technology for sintering calcium phosphate to manufacture a calcium phosphate sintered body and suppressing generation of calcium oxide when calcium phosphate is sintered, there is provided a process for manufacturing a sintered calcium phosphate molded body is characterized by including a step for heating a composition containing at least a composite of calcium phosphate fine particles and polyether and sintering the calcium phosphate fine particles.

16 Claims, 8 Drawing Sheets

(51) Int. Cl.
    *C04B 38/06*     (2006.01)
    *C04B 35/634*     (2006.01)
    *C04B 35/626*     (2006.01)
    *B01J 20/30*     (2006.01)
    *A61L 31/00*     (2006.01)
    *B01J 20/04*     (2006.01)
    *C04B 111/00*     (2006.01)

(52) U.S. Cl.
    CPC ......... *C01B 25/32* (2013.01); *C04B 35/6263* (2013.01); *C04B 35/63424* (2013.01); *C04B 35/63488* (2013.01); *C04B 38/067* (2013.01); *C01P 2002/72* (2013.01); *C01P 2002/88* (2013.01); *C01P 2004/03* (2013.01); *C01P 2004/62* (2013.01); *C01P 2004/64* (2013.01); *C04B 2111/00836* (2013.01); *C04B 2235/3212* (2013.01); *C04B 2235/447* (2013.01); *C04B 2235/5445* (2013.01); *C04B 2235/5454* (2013.01)

(56) References Cited

U.S. PATENT DOCUMENTS

| | | | | |
|---|---|---|---|---|
| 6,340,648 | B1* | 1/2002 | Imura | ..................... A61L 27/12 |
| | | | | 106/35 |
| 2009/0191111 | A1 | 7/2009 | Oh et al. | |
| 2010/0152317 | A1* | 6/2010 | Aizawa | ................. A61L 27/425 |
| | | | | 523/115 |
| 2012/0136088 | A1* | 5/2012 | Aizawa | ................. A61L 27/425 |
| | | | | 523/115 |
| 2013/0028972 | A1* | 1/2013 | Schwier | ................. A61P 25/36 |
| | | | | 424/465 |
| 2017/0058116 | A1* | 3/2017 | Ando | ................. C08G 18/6225 |

FOREIGN PATENT DOCUMENTS

| | | |
|---|---|---|
| JP | H09-299472 A | 11/1997 |
| JP | 2000-302567 A | 10/2000 |
| JP | 2003-146773 A | 5/2003 |
| JP | 2004-33589 A | 2/2004 |
| JP | 2004-275202 A | 10/2004 |
| JP | 2005-001943 A | 1/2005 |
| JP | 2007-090338 A | 4/2007 |
| JP | 2010-18459 A | 1/2010 |
| JP | 2011-42516 A | 3/2011 |
| JP | 2012-197203 A | 10/2012 |

OTHER PUBLICATIONS

International Preliminary Report on Patentability issued in International Application No. PCT/JP2016/076347; dated Mar. 29, 2018 (7 pages).
Extended European Search Report issued in European Application No. 16846345.3, dated Apr. 26, 2019 (7 pages).
International Search Report of the International Searching Authority issued in PCT/JP2016/076347 dated Oct. 11, 2016 (5 pages).
Written Opinion of the International Searching Authority issued in PCT/JP2016/076347 dated Oct. 11, 2016 (4 pages).

* cited by examiner

SINTERED CALCIUM PHOSPHATE MOLDED BODY AND PROCESS FOR MANUFACTURING THE SAME

TECHNICAL FIELD

The present invention relates to a novel sintered calcium phosphate molded body and a process for manufacturing the same.

BACKGROUND ART

Calcium phosphate including hydroxyapatite (HAp) adsorbs microorganisms and viruses, is also applicable to an insulating film of an electronic part or the like, and is a useful material.

Here, various attempts have been made to manufacture a molded body of a hydroxyapatite sintered body by sintering hydroxyapatite by a special method. For example, regarding a porous sintered body, Patent Literature 1 proposes a method for mixing hydroxyapatite particles and thermally decomposable particles to obtain a mixture and sintering the mixture. According to this method, the thermally decomposable particles are burned off, and the spots where the thermally decomposable particles were present become voids such that a porous body is obtained. In addition, Patent Literature 2 proposes a method for preparing a mixture obtained by adding a specific component (a component that has a frost pillar shape when being cooled) to hydroxyapatite, and cooling the mixture. According to this method, as a result of frost pillarization of the specific component, a porous body is obtained. Furthermore, Patent Literature 3 proposes a method for mixing air with hydroxyapatite particles and mechanically stirring the mixture to obtain a foam composition in which bubbles are present between the hydroxyapatite particles, and heating the composition to obtain a porous molded body. Regarding a dense sintered body, Patent Literature 4 proposes a method for forming a dense hydroxyapatite layer by applying a salt obtained from aminopolycarboxylic acid and a calcium compound to a surface of a substrate and sintering the salt. Patent Literature 5 proposes technology for forming a hydroxyapatite layer using sputtering.

CITATION LIST

Patent Literature

Patent Literature 1: JP 2012-197203 A
Patent Literature 2: JP 2010-18459 A
Patent Literature 3: JP 2000-302567 A
Patent Literature 4: JP 2004-33589 A
Patent Literature 5: JP 2007-090338 A

SUMMARY OF INVENTION

Technical Problem

Here, a sintered body obtained by a conventional method including Patent Literatures 1 to 5 contains a considerable amount of calcium oxide in a calcium phosphate phase. Due to this, there are concerns about inviting various problems such as reduction in mechanical strength, alkali generation due to dissolution of calcium oxide upon contact with water (this may cause problem such as adsorption or denaturation in mass transfer), and variation in electric/electronic behavior such as a resistance value. Therefore, an object of the present invention is to provide technical solution for sintering calcium phosphate to manufacture a calcium phosphate sintered body and suppressing generation of calcium oxide when calcium phosphate is sintered. As for a porous body, there is an additional problem. A porous molded body of a calcium phosphate sintered body according to prior art including Patent Literatures 1 to 3 has a pore of a small pore diameter (for example, nanosize) and application thereof is limited disadvantageously. Therefore, a secondary object of the present invention is to provide a porous molded body of a calcium phosphate sintered body, having not only a pore with a small pore diameter as in prior art but also a pore with a pore diameter much larger than that according to prior art.

Solution to Problem

As a result of repeated verification on various raw materials, various manufacturing conditions, and the like, the present inventors have found that the above problems can be solved by using a specific raw material, and have completed the present invention. Specifically, the present invention is as follows.

The present invention (1) is a process for manufacturing a sintered calcium phosphate molded body, characterized by including a step of heating a composition containing at least a composite of calcium phosphate fine particles and polyether, and a step of sintering the calcium phosphate fine particles.

The present invention (2) is the manufacturing process according to the invention (1), in which the calcium phosphate fine particles have an average particle diameter of 10 to 500 nm.

The present invention (3) is the manufacturing process according to the invention (1) or (2), in which the composition contains thermally decomposable particles.

The present invention (4) is the manufacturing process according to the invention (3), in which the thermally decomposable particles are a hydrophilic polymer.

The present invention (5) is the manufacturing process according to the invention (3) or (4), in which the thermally decomposable particles are a (meth)acrylic acid polymer or a derivative thereof.

The present invention (6) is the manufacturing process according to any one of the inventions (1) to (5), in which the sintered calcium phosphate molded body comprises or is formed of hydroxyapatite.

The present invention (7) is the manufacturing process according to the invention (6), in which the sintered calcium phosphate molded body contains hydroxyapatite in an amount of 80% by mass or more based on the total mass of the sintered calcium phosphate molded body.

Advantageous Effects of Invention

The present invention can provide technology for suppressing generation of calcium oxide even when calcium phosphate is sintered in technology for sintering calcium phosphate to manufacture a calcium phosphate sintered body. In the present invention, a hydroxyapatite molded body having a porous form is a porous molded body of a hydroxyapatite molded body having both a pore with a small pore diameter as in prior art and a pore with a pore diameter much larger than that in prior art. Thus, a hydroxyapatite molded body according to the present invention can be applied to many applications. Particularly, the manufacturing process according to the present invention can realize a pore diameter better than a theoretical pore diameter (specifically, the size of a thermally decomposable particle, that is, a void where the thermally decomposable particle was present as a result of decomposition of the thermally decomposable particle by heating).

DESCRIPTION OF EMBODIMENTS

Hereinafter, a sintered calcium phosphate molded body according to the present invention, a process for manufacturing the sintered calcium phosphate molded body according to the present invention, applications of the sintered calcium phosphate molded body according to the present invention, and the like will be sequentially described.

<<Sintered Calcium Phosphate Molded Body>>
<Component>

The sintered calcium phosphate molded body according to the present invention contains or is formed of calcium phosphate. Here, examples of calcium phosphate include hydroxyapatite, β-tricalcium phosphate (TCP), α-TCP, and a mixture thereof. Incidentally, in a case where the sintered calcium phosphate molded body according to the present invention is used in applications requiring water insolubility, protein adsorption properties, and the like, calcium phosphate is preferably hydroxyapatite (for example, the content of hydroxyapatite is preferably 80% by mass or more, and more preferably 90% by mass or more based on the total mass of a sintered calcium phosphate molded body). Here, the content of hydroxyapatite can be measured by XRD.

<Non-Contained Component>

The sintered calcium phosphate molded body according to the present invention substantially contains no calcium oxide as described later {i.e. a peak of calcium oxide (2θ=37.34°) does not appear when a crystal structure of the sintered calcium phosphate molded body is investigated by XRD}.

<Pore Diameter>

The sintered calcium phosphate molded body according to the present invention may be a porous body or a dense body. Here, the dense body refers to one having a porosity of 5% or less (conversely, the porous body refers to one having a porosity of more than 5%). Here, the porosity is a value calculated by {(volume×theoretical weight density of constituent component−actual weight)/(volume×theoretical weight density of constituent component)}×100(%). Note that the sintered calcium phosphate molded body is prefer-ably a porous body in applications requiring a large surface area. Here, in a case of a porous body, a preferable sintered calcium phosphate molded body has fine pores (preferably, average pore diameter=10 to 1000 nm), and large pores (preferably average pore diameter=50 to 500 μm). Here, the average pore diameter is calculated from an image taken by a scanning electron microscope (SEM). Incidentally, as for the fine pores, major diameters of all the fine pores existing in a field of view of an image taken at 10,000 times of a magnification are measured, and an average value thereof is taken as an average pore diameter. As for the large pores, major diameters of all the pores existing in a field of view of an image taken at 30 times are measured, and an average value thereof is obtained as an average pore diameter.

<<Process for Manufacturing Sintered Calcium Phosphate Molded Body>>

Next, a process for manufacturing a sintered calcium phosphate molded body according to the present invention will be described in detail.

<Raw Materials Used>

{Polyether-Modified Calcium Phosphate Fine Particles}

One of raw materials used in the manufacturing process is polyether-modified calcium phosphate fine particles (a composite or complex of calcium phosphate fine particles and polyether), and preferably polyether-modified calcium phosphate nanoparticles. Hereinafter, an aspect in which polyether-modified calcium phosphate nanoparticles are used as a preferable example will be described in detail. The particles are obtained by chemically bonding polyether to surfaces of calcium phosphate nanoparticles. Note that a fact polyether is chemically bonded can be confirmed by a fact that a peak different from or not appearing with these components alone appears in polyether-modified calcium phosphate nanoparticles in TG-DTA analysis or Fourier transform infrared spectroscopy (FT-IR) analysis. Hereinafter, each constituent component of the particles and a manufacturing process will be described.

(Polyether)

Polyether is a polymer having a plurality of ether bonds in a main chain thereof. Polyether is obtained by ring-opening polymerization of a cyclic ether (for example, crown ether), self-condensation of a glycol (for example, polyethylene glycol (PEG)), oxidation polymerization of a diol compound, or the like. Specific examples of the polyether are not particularly limited, but include polyethylene glycol, polyethylene oxide, polypropylene glycol, polypropylene oxide, pentaethylene glycol, polytetramethylene oxide, polyphenylene ether, pentaethylene glycol monododecyl ether, and a polysaccharide such as dextrin or cyclodextrin. Here, the polyether in the present invention also includes an aspect in which a terminal OH group is blocked (for example, by chemical modification with an alkyl or a saccharide). Here, a role of the polyether (function to prevent from generating calcium oxide) is presumed as follows. First, it is considered that polyether bonded to calcium phosphate nanoparticles functions to weakly bond the calcium phosphate particles to each other {as a result, it is possible to obtain a slurry in which agglomeration of the nanoparticles (lumps) is inhibited}. By heating the slurry thus obtained, dehydration progresses while homogeneity is maintained, and fusion is accelerated by approach of primary particles. Based on this principle, it is presumed that the calcium phosphate nanoparticles are bonded to each other at a temperature lower than a usual or conventional sintering temperature. That is, in a heating environment at a temperature lower than a temperature at which calcium phosphate turns into calcium oxide, calcium phosphate particles have been already aggregated to produce a dense structure. Therefore, even in this situation, mass transfer between the calcium phosphate particles hardly occurs (that is, decomposition of calcium phosphate to calcium oxide is suppressed). As a result, it is considered that a calcium phosphate homogeneous phase including little calcium oxide is formed.

(Calcium Phosphate Nanoparticles)

The calcium phosphate nanoparticles may be sintered or non-sintered. Note that the calcium phosphate nanoparticles can be manufactured, for example, according to description in JP 5043436 B2. Here, an average particle diameter of the calcium phosphate nanoparticles is preferably 10 nm to 500 nm, more preferably 15 nm to 450 nm, and most preferably 20 nm to 400 nm. A variation coefficient of a particle diameter in a primary particle group including or consisting of primary particles is preferably 20% or less, more preferably 18% or less, and most preferably 15% or less. Note that it is only required to calculate the particle diameter and the variation coefficient of the primary particle by measuring particle diameters of at least 100 primary particles using a dynamic light scattering method or an electron microscope. Here, the "variation coefficient" is a value indicating variation of particle diameters among particles which can be calculated by standard deviation/average particle diameter× 100(%).

(Manufacturing Process)

Polyether-modified calcium phosphate nanoparticles can be manufactured, for example, by adding polyether (for example PEG) and calcium phosphate nanoparticles (for example, hydroxyapatite nanoparticles) into water to obtain a mixture, and continuously stirring the resulting mixture at a temperature of 5 to 100° C. for 10 to 120 minutes.

Here, a ratio of an addition amount (mass) of polyether based on an addition amount (mass) of calcium phosphate nanoparticles is preferably 0.1 equivalent to 10 equivalents, and more preferably 0.5 equivalent to 2 equivalents.

{Thermally Decomposable Particles}

(Degree of Swelling)

When a porous body of the sintered calcium phosphate molded body according to the present invention is manufactured, thermally decomposable particles may be preferably used. Note that the term "thermally decomposable particles" refers to particles which are thermally decomposed at a sintering temperature (for example, 200 to 2000° C.) described later. Here, the thermally decomposable particles used in the present invention may be or be made of a hydrophilic polymer. Here, the term "hydrophilic" means what hydrophilic means in general, and means, for example, that the degree of swelling with respect to water is 5 to 10,000 times (mass ratio). Note that a method to measure the degree of swelling is as follows. A bulk density of thermally decomposable particles before swelling is measured. Water is added to the thermally decomposable particles in accordance with conditions for adding water at the time of preparation of a molded body. A generated supernatant is removed. Thereafter, a change in mass between before and after adding water is taken as the degree of swelling.

(Component)

Preferable thermally decomposable particles are a (meth) acrylic acid polymer or a derivative thereof. Examples of the derivative include a (meth)acrylic acid polymer of which a carboxyl group is modified and a crosslinked product of a (meth)acrylic acid polymer. Here, particularly preferable thermally decomposable particles are a crosslinked product of an acrylic acid polymer with a saccharide.

(Particle Diameter)

The thermally decomposable particles (dry state) according to the present invention preferably have an average particle diameter larger than an average particle diameter of calcium phosphate nanoparticles. Specifically, the thermally decomposable particles (dry state) used in the present manufacturing process preferably have an average particle diameter of 10 to 1,000 nm, more preferably of 50 to 800 nm. Incidentally, here, the "average particle diameter" is intended to mean an average of diameters of individual particles in the entire particle group. However, in a case of particles having a major diameter and a minor diameter different from each other, such as rod-shaped particles or fiber-shaped particles, the "average particle diameter" means an average of major diameters of individual particles in the entire particle group.

<Manufacturing Process>

The process for manufacturing the sintered calcium phosphate molded body according to the present invention includes a step of sintering the calcium phosphate nanoparticles, heating a composition (containing also thermally decomposable particles when a porous body is manufactured) containing at least the above-mentioned composite (composite of calcium phosphate nanoparticles and polymer), and decomposing thermally decomposing polymer (also thermally decomposable particles in case of containing the thermally decomposable particles). In this case, a sintering temperature is preferably 200 to 2000° C., and more preferably 300 to 1800° C. Furthermore, sintering time is preferably more than 0 hour and 24 hours or less, and more preferably more than 0 hour and 18 hours or less. In a case of manufacturing a porous body, the total amount of the composite and the thermally decomposable particles: the amount of the thermally decomposable particles (mass ratio) is preferably 10:1 to 30:1, and more preferably 15:1 to 20:1.

Here, in the process to manufacture a sintered calcium phosphate molded body according to the present invention, a liquid medium is not particularly limited as long as it can be blended to the composition. Examples of such a liquid medium include water (for example, deionized water or ultrapure water), methanol, ethanol, isopropanol, acetone, N,N-dimethylformamide, dimethylsulfoxide, and a mixture thereof. Another known component may be added to the composition, as necessary.

(Process for Manufacturing Hydroxyapatite Molded Body)

A process for manufacturing a hydroxyapatite molded body, among sintered calcium phosphate molded bodies, will be described. The process for manufacturing a hydroxyapatite molded body may be, for example, (1) a process comprising sintering a composite of hydroxyapatite nanoparticles and polyether as a raw material at 300 to 1400° C. (a temperature lower than a melting point of hydroxyapatite), or (2) a process comprising sintering a composite of α-TCP nanoparticles and polyether as a raw material at 300 to 1800° C. to obtain a sintered body, and then adding water to the sintered body.

<<Application of Sintered Calcium Phosphate Molded Body>>

The sintered calcium phosphate molded body according to the present invention substantially contains no calcium oxide as described above. Therefore, even when the sintered calcium phosphate molded body comes into contact with water, there is no problem of reduction in mechanical strength due to a heterogeneous phase or alkalization due to dissolution of calcium oxide. Therefore, the sintered calcium phosphate molded body is effective in a field requiring mechanical strength and/or a field in which alkalization is regarded as a problem (for example, in a field of electric/electronic materials, corrosion of a joint surface is caused disadvantageously). Specifically, for example, a dense body of the sintered calcium phosphate molded body according to an aspect of the present invention can be used for a protective film on an electrode surface of a sensor or the like, an insulator, a separator of a battery, an ion conductor, and a carrier of a peptide or a physiologically active substance. On the other hand, a porous body of the sintered calcium phosphate molded body according to an aspect of the present invention preferably has fine pores (preferably, average pore diameter=10 to 100 nm) and large pores (preferably, average pore diameter=50 to 500 µm) in addition to the above characteristics. That is, a specific surface area is very large. Furthermore, the porous body of the sintered calcium phosphate molded body according to an aspect of the present invention also has micro-sized pores as well as nano-sized pores as in a conventional sintered calcium phosphate molded body. Therefore, in consideration of the above characteristics, for example, in a case of use as a filter, the porous body of the sintered calcium phosphate molded body according to an aspect of the present invention can be used as a water-insoluble filter having a low pressure loss and high protein adsorption ability. Specific examples thereof include a filter for removing microorganisms and viruses, and a filter for water purification. The porous body of the sintered calcium phosphate molded body according to an aspect of the present invention is also useful as a barrier used in a sensor for detecting electrons and mass transfer. Furthermore, in a case where the sintered calcium phosphate molded body according to the present invention is a hydroxyapatite molded body, the hydroxyapatite molded body is hardly dissolved in water, and therefore is suitable for a medical instrument to be applicable to a living body, for example.

EXAMPLES (Preparation of Hydroxyapatite Nanoparticles)

Dodecane [$CH_3(CH_2)_{10}CH_3$] was used as a continuous oil phase, and pentaethylene glycol dodecyl ether [($CH_3(CH_2)_{10}CH_2O(CH_2CH_2O)_4CH_2CH_2OH$] having a cloud point of 31° C. was used as a nonionic surfactant. At room temperature, 40 ml of a continuous oil phase containing 0.5 g of the nonionic surfactant was prepared. Next, 10 ml of 2.5 mol/l calcium hydroxide [$Ca(OH)_2$] dispersing liquid was added to the continuous oil phase to prepare a water-in-oil type liquid (W/O liquid). While the W/O liquid was stirred, 10 ml of 1.5 mol/l potassium dihydrogen phosphate [($KH_2PO_4$)] solution was added thereto. A reaction was allowed to proceed for 24 hours under stirring at room temperature. Next, the resulting reaction product was separated and washed by centrifugation to obtain a primary particle of hydroxyapatite (HAp). A particle diameter of the primary particle in the hydroxyapatite (HAp) generally or substantially fell within a range between 10 nm to 100 nm (the average particle diameter was 23 nm), and a variation coefficient of the particle diameter in the primary particle was 11% or less.

(Preparation of HAp Nanoparticle/PEG Composite)

Figure 1:
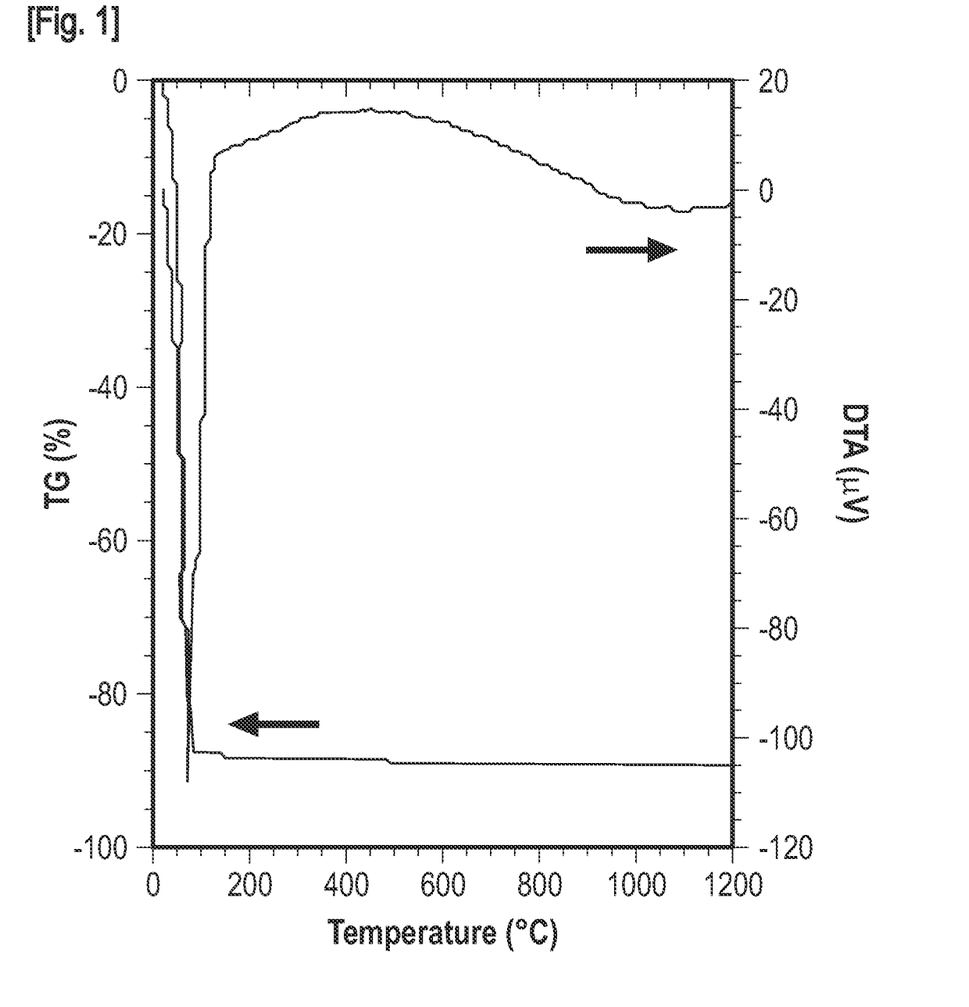
FIG. 1 is a chart of thermogravimeter-differential thermal analyzer (TG-DTA) of HAp before compositing.
Figure 2:
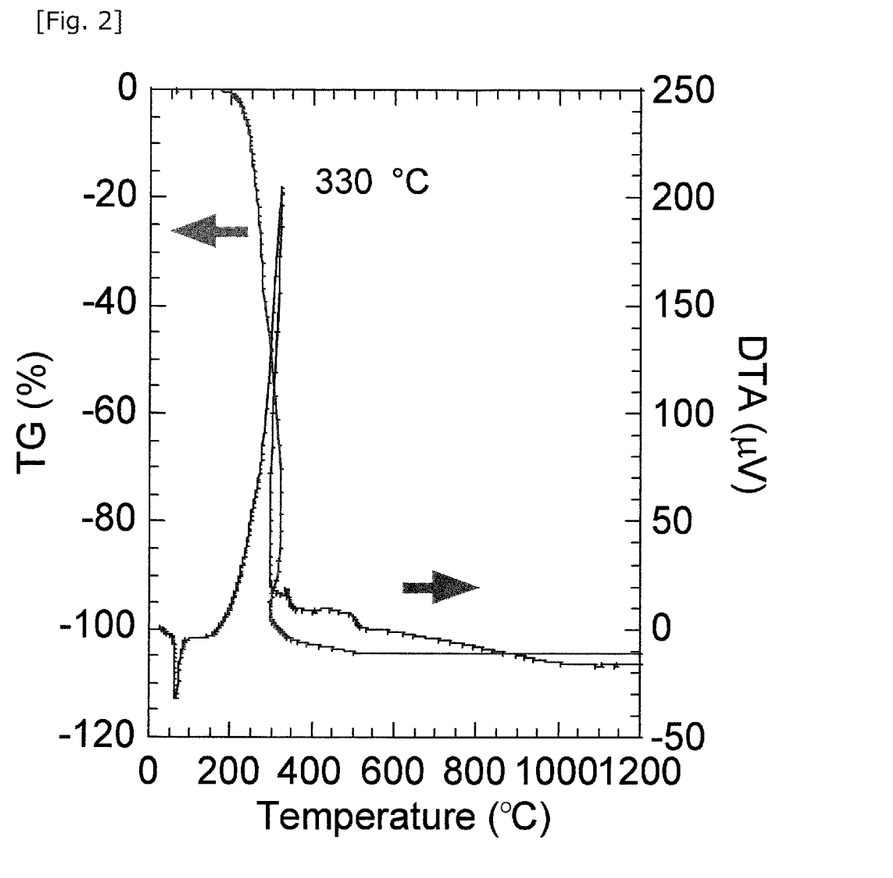
FIG. 2 is a chart (TG-DTA) of PEG before compositing.
Figure 3:
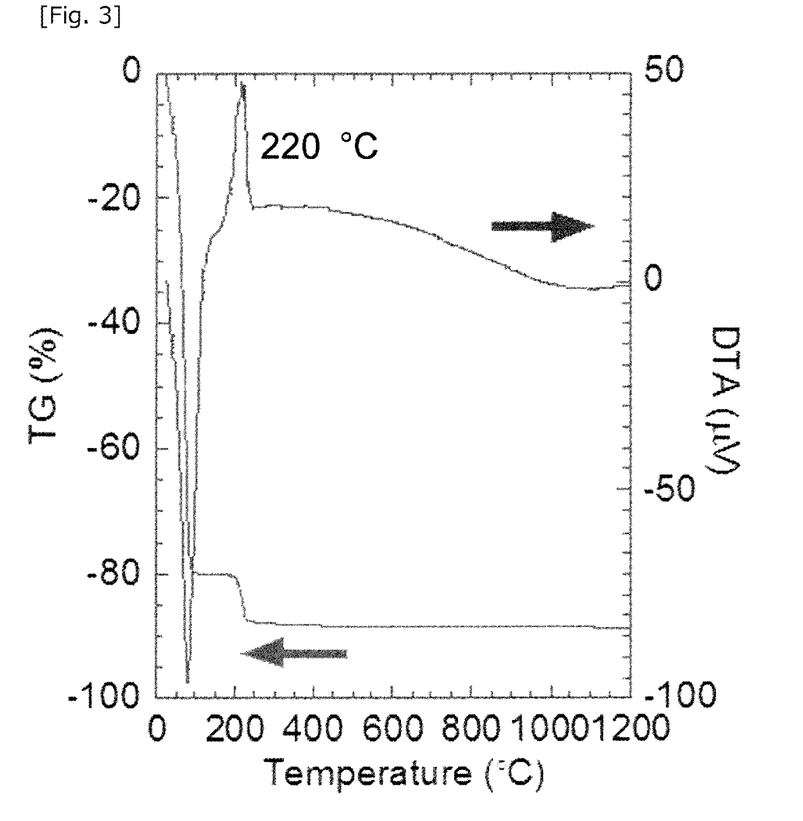
FIG. 3 is a chart (TG-DTA) of a HAp/PEG composite.

Under a nitrogen gas atmosphere, 50 g of HAp nanoparticles and 50 g of polyethylene glycol (PEG 3400) were added to 500 ml of deionized water, and the resulting mixture was kept at 80° C. for about 1 hour to obtain a dispersion containing a HAp/PEG composite. Note that HAp and PEG before compositing and the HAp/PEG composite were thermogravimetrically measured and compared with each other using thermogravimetry. Here, FIG. 1 is a chart of HAp before compositing. FIG. 2 is a chart of PEG before compositing. FIG. 3 is a chart of the HAp/PEG composite. FIGS. 1 to 3 indicate that an exothermic peak of the HAp/PEG composite shifted to a lower temperature side as compared with HAp and PEG before compositing. From this fact that an exothermic peak was observed at a temperature different from a characteristic inherently exhibited by HAp and PEG, it is understood that compositing has occurred.

(Preparation of Porous Material)

Manufacturing Example 1 (Raw Material: HAp)

Figure 4:
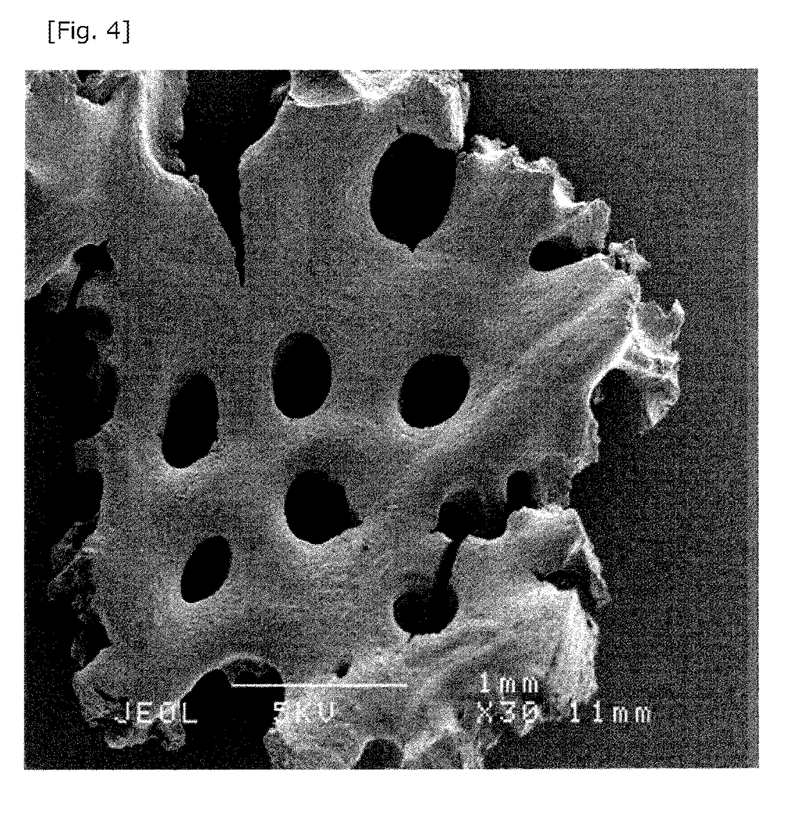
FIG. 4 is a scanning electron microscope (SEM) photograph of a sintered calcium phosphate molded body (porous material) according to Manufacturing Example 1.
Figure 5:
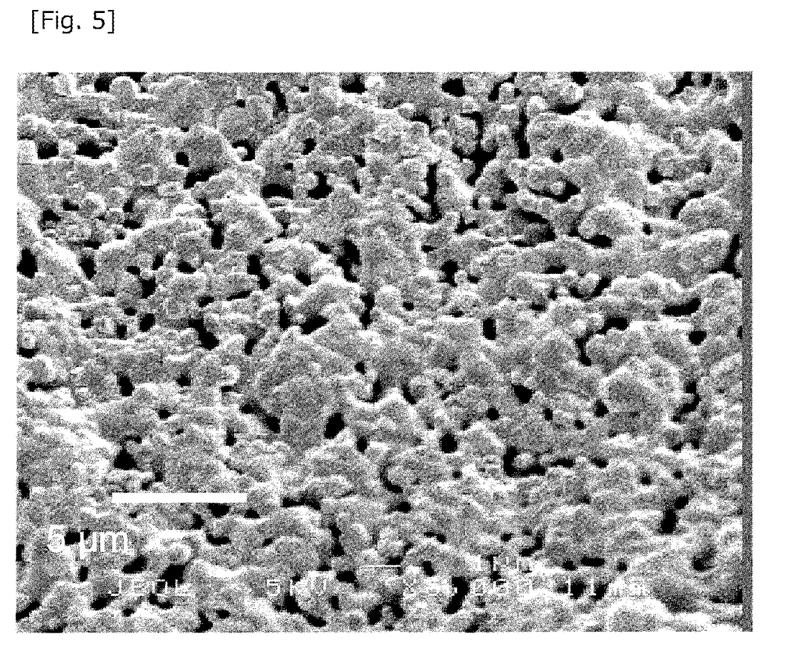
FIG. 5 is a SEM photograph of the sintered calcium phosphate molded body (porous material) according to Manufacturing Example 1.
Figure 6:
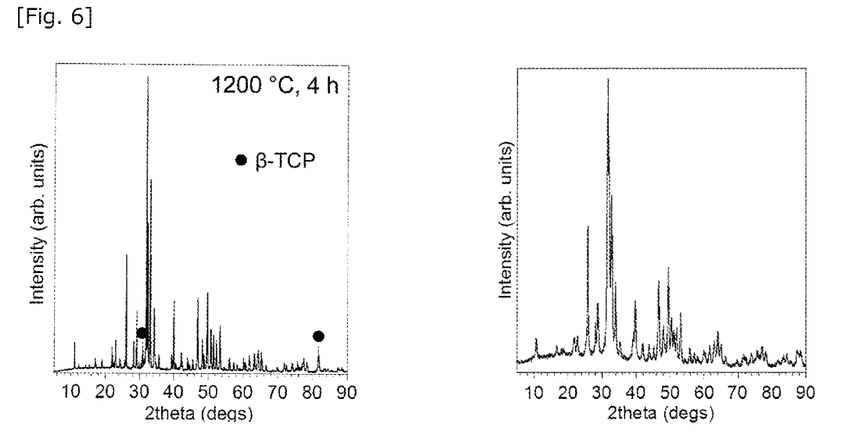
FIG. 6 is an X-ray diffraction (XRD) profile before and after sintering in Manufacturing Example 1 (left: after sintering, right: before sintering).

To a solution obtained by dissolving 1 g of Carbopol (trade name: prepared by Lubrizol Advanced Materials, Inc) of particles formed of a crosslinked acrylic acid polymer in 50 ml of deionized water, 19 g of the dispersion (dispersion containing HAp/PEG composite) was mixed and stirred at 24° C. for 12 hours or more. Thereafter, the solution was heat-treated at 1200° C. for 4 hours to obtain a porous material. FIGS. 4 and 5 are SEM photographs of the present porous material (different from each other in magnification). From FIGS. 4 and 5, it can be confirmed that pores of micrometer order and nanometer order are open. Note that an average pore diameter of the micrometer-order pores was 280 µm and an average pore diameter of the nanometer-order pores was 200 nm. A porosity was 11%. FIG. 6 is an X-ray diffraction chart before and after sintering (left: after sintering, right: before sintering). From FIG. 6, it was confirmed that most peaks (80% by mass or more) were derived from hydroxyapatite under these conditions although some peaks derived from β-TCP appeared (as a result of performing the experiment a plurality of times, a peak derived from β-TCP was at most 20% by mass). In addition, no peak derived from calcium oxide was confirmed.

Manufacturing Example 2 (Raw Material: HAp)

Figure 7:
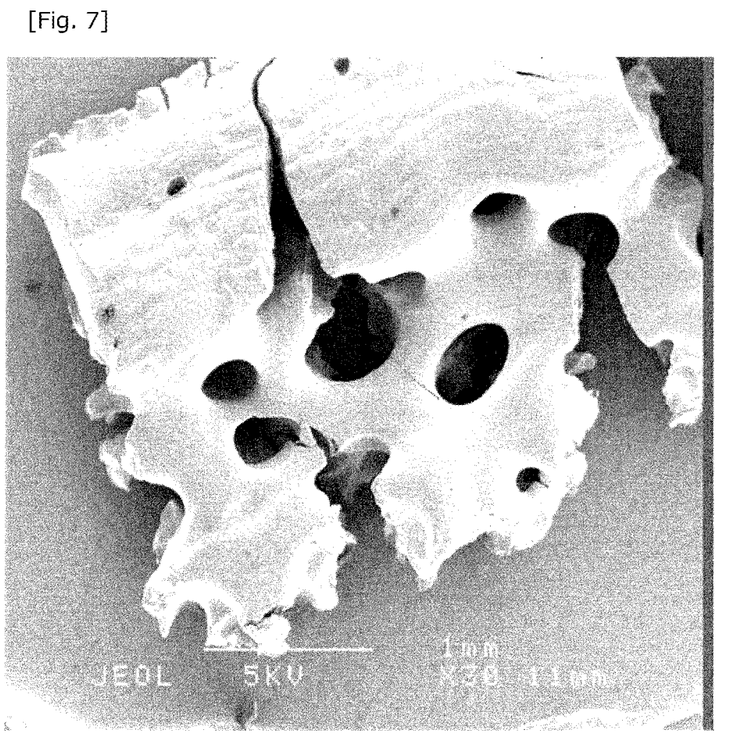
FIG. 7 is a SEM photograph of a sintered calcium phosphate molded body (porous material) according to Manufacturing Example 2.

A porous material was obtained in a similar manner to Manufacturing Example 1 except that the use amount of Carbopol in Manufacturing Example 1 was changed to 0.1 g. FIG. 7 is a SEM photograph of the present porous material. The photograph indicates that pores of several hundred µm are opened (although not illustrated, it was confirmed that pores in nanometer order were opened). A porosity was more than 5%. Note that the amount of hydroxyapatite was 84% by mass and the amount of β-TCP was 16% by mass in the porous material. In addition, no peak derived from calcium oxide was confirmed.

Manufacturing Example 3 (Raw Material: HAp)

Figure 8:
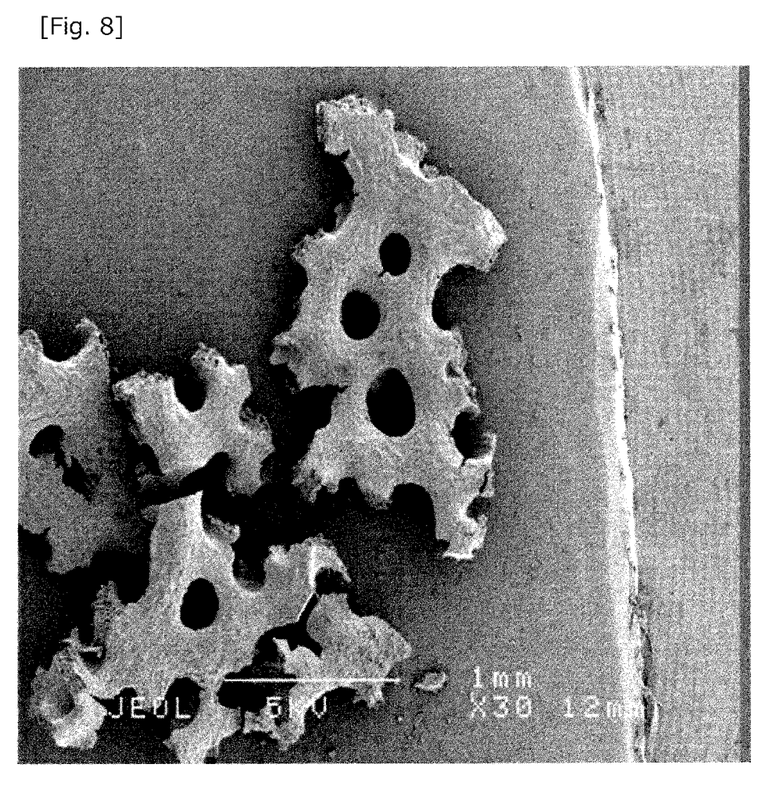
FIG. 8 is a SEM photograph of a sintered calcium phosphate molded body (porous material) according to Manufacturing Example 3.

A porous material was obtained in a similar manner to Manufacturing Example 1 except that the use amount of Carbopol in Manufacturing Example 1 was changed to 2.5 g. FIG. 8 is a SEM photograph of the present porous material. The photograph indicates that pores of several hundred µm are opened (although not illustrated, it was confirmed that pores in nanometer order were opened). A porosity was more than 5%. Although not illustrated, it was confirmed that the present porous material contained hydroxyapatite in an amount of more than 80% by mass and contained no calcium oxide.

Preparation of α-TCP Fine Particles/PEG Composite

Under a nitrogen gas atmosphere, 20 g of α-TCP fine particle and 20 g of polyethylene glycol (PEG 3400) were added to 200 ml of deionized water, and the resulting mixture was kept at 80° C. for about 1 hour to obtain a dispersion containing an α-TCP/PEG composite. Note that it was confirmed that α-TCP particles were chemically bonded to PEG in accordance with the process in Manufacturing Example 1.

Manufacturing Example 4 (Raw Material: α-TCP)

To a solution obtained by dissolving 1 g of Carbopol (trade name: prepared by Lubrizol Advanced Materials, Inc) which are particles formed of a crosslinked acrylic acid polymer in 50 ml of deionized water, 19 g of the dispersion (dispersion containing an α-TCP/PEG composite) was mixed and stirred at 24° C. for 12 hours or more. Thereafter, the solution was heat-treated at 1200° C. for 4 hours to obtain a porous material in which formation of pores could be visually confirmed (although not illustrated, it was confirmed that pores in micrometer order and nanometer order were open). A porosity was more than 5%.

(Preparation of Dense Body Material)

Manufacturing Example 5

20 g of the dispersion (dispersion containing a HAp/PEG composite) was heat-treated at 1200° C. for 4 hours to obtain a dense body material. This dense body material had a porosity of 2%. Although not illustrated, it was confirmed that the present porous material contained hydroxyapatite in an amount of more than 80% by mass and contained no calcium oxide.

The invention claimed is:

1. A process for manufacturing a sintered calcium phosphate molded body, the process comprising heating a composition comprising thermally decomposable particles, a liquid medium, and a dispersion comprising a composite of calcium phosphate fine particles and polyether,
    wherein the heating is performed to sinter the calcium phosphate fine particles,
    wherein the calcium phosphate fine particles have an average particle diameter ranging from 10 to 500 nm,
    wherein the thermally decomposable particles are a hydrophilic polymer, and
    wherein the liquid medium is selected from the group consisting of water, methanol, ethanol, isopropanol, acetone, N,N-dimethylformamide, dimethylsulfoxide, and a combinations thereof.

2. The manufacturing process according to claim 1, wherein the thermally decomposable particles are a (meth) acrylic acid polymer or a derivative thereof.

3. The manufacturing process according to claim 1, wherein the sintered calcium phosphate molded body comprises hydroxyapatite.

4. The manufacturing process according to claim 3, wherein the sintered calcium phosphate molded body comprises hydroxyapatite in an amount of 80% by mass or more based on a total mass of the sintered calcium phosphate molded body.

5. The manufacturing process according to claim 1,
    wherein a peak of calcium oxide does not appear when a crystal structure of the sintered calcium phosphate molded body is measured by XRD,
    wherein the peak of calcium oxide is represented by 2θ=37.34° when measured by XRD.

6. The manufacturing process according to claim 1, wherein the sintered calcium phosphate molded body has a porosity of 5% or less.

7. The manufacturing process according to claim 1, wherein the sintered calcium phosphate molded body has a porosity of more than 5%.

8. The manufacturing process according to claim 1, wherein the polyether is one compound selected from the group consisting of polyethylene glycol, polyethylene oxide, polypropylene glycol, polypropylene oxide, pentaethylene glycol, polytetramethylene oxide, polyphenylene ether, pentaethylene glycol monododecyl ether, and a polysaccharide, wherein the polysaccharide is selected from the group consisting of dextrin and cyclodextrin.

9. The manufacturing process according to claim 1, wherein the process comprises adding the polyether and the calcium phosphate fine particles into water to obtain a mixture of the calcium phosphate fine particles and the polyether, and continuously stirring the mixture of the calcium phosphate fine particles and the polyether at a temperature ranging from 5 to 100° C. for a time ranging from 10 to 120 minutes to obtain the composite of the calcium phosphate fine particles and the polyether.

10. The manufacturing process according to claim 9, wherein a ratio of an addition amount by mass of the polyether to an addition amount by mass of the calcium phosphate fine particles is from 0.1:1 to 10:1.

11. The manufacturing process according to claim 1, wherein the thermally decomposable particles comprise a crosslinked product of a (meth)acrylic acid polymer.

12. The manufacturing process according to claim 11, wherein the crosslinked product of the (meth)acrylic acid polymer comprises a crosslinked product of an acrylic acid polymer with a saccharide.

13. The manufacturing process according to claim 1, wherein, before swelling, the thermally decomposable particles have an average particle diameter larger than an average particle diameter of the calcium phosphate fine particles.

14. The manufacturing process according to claim 1, wherein a sintering temperature of the heating the composition is from 200 to 2000° C.

15. The manufacturing process according to claim 1, wherein a sintering time of the heating the composition is from 0 hour to 24 hours.

16. The manufacturing process according to claim 1, wherein a ratio of a total amount of the composite of the calcium phosphate fine particles and the polyether and the thermally decomposable particles by mass to an amount of the thermally decomposable particles by mass is from 10:1 to 30:1.

* * * * *